United States Patent [19]
Villeponteau et al.

[11] Patent Number: 5,972,605
[45] Date of Patent: Oct. 26, 1999

[54] ASSAYS FOR REGULATORS OF MAMMALIAN TELOMERASE EXPRESSION

[75] Inventors: Bryant Villeponteau, San Carlos; Calvin Harley, Palo Alto, both of Calif.

[73] Assignee: Geron Corporation, Menlo Park, Calif.

[21] Appl. No.: 08/714,482

[22] Filed: Sep. 16, 1996

Related U.S. Application Data

[63] Continuation-in-part of application No. 08/521,634, Aug. 31, 1995, abandoned, which is a continuation-in-part of application No. 08/482,115, Jun. 7, 1995, Pat. No. 5,776,679, which is a continuation-in-part of application No. 08/472,802, Jun. 7, 1995, which is a continuation-in-part of application No. 08/330,123, Oct. 27, 1994, Pat. No. 5,583,016, which is a continuation-in-part of application No. 08/272,102, Jul. 7, 1994, abandoned.

[51] Int. Cl.$^6$ .............................. C12Q 1/68; C12P 19/34; C12N 9/12; C07H 21/04
[52] U.S. Cl. .............................. 435/6; 435/91.2; 435/194; 435/252.3; 435/320.1; 536/23.1; 536/23.2; 536/24.31; 536/24.33
[58] Field of Search .............................. 435/6, 91.2, 194, 435/252.3, 320.1; 536/24.31, 24.33, 23.1, 23.2

[56] References Cited

U.S. PATENT DOCUMENTS 5,583,016 12/1996 Villeponteau et al. ................. 435/91.3
5,645,986 7/1997 West et al. ................................ 435/6

FOREIGN PATENT DOCUMENTS

95/13382 5/1995 WIPO .
96/01835 1/1996 WIPO .
WO 96/01614 1/1996 WIPO .

OTHER PUBLICATIONS

Feng, et al., "The RNA Component of Human Telomerase", *Science*, 269:1236 (1995).
Kim, et al., "Specific Association of Human Telomerase Activity with Immortal Cells and Cancer", *Science*, 266:2011 (1994).
Grider, et al., "Telomeres, Telomerase and Cancer", *Scientific American*, Feb. 1996, pp. 92–97.
Harley, et al., "Telomeres and telomerase in aging and cancer", *Current Opinion in Genetics and Development*, 5:249–255 (1995).
Harley, "Telomeres and Aging: Fact, Fancy, And The Future", *The Journal of NIH Research*, 7:64–68 (1995).
Villeponteau, "The RNA components of human and mouse telomerases", *Cell & Developmental Biology*, 7:15–21 (1996).

*Primary Examiner*—Robert A. Wax
*Assistant Examiner*—Tekchand Saidha

[57] ABSTRACT

Telomerase reporter constructs suitable for use in reporting transcriptional activity of a mammalian telomerase gene transcription regulatory region contain a transcription regulatory region of a mammalian telomerase gene operably linked to a reporter polynucleotide sequence.

20 Claims, 3 Drawing Sheets

A.

B.

ered, sensitive basis for reporting transcription levels.

ASSAYS FOR REGULATORS OF MAMMALIAN TELOMERASE EXPRESSION

CROSS-REFERENCE TO RELATED APPLICATION

This application is a continuation-in-part of U.S. Ser. No. 08/521,634, filed Aug. 31, 1995, now abandoned, which is a continuation-in-part of U.S. Ser. No. 08/482,115, filed Jun. 7, 1995, now U.S. Pat. No. 5,776,679, which is a continuation-in-part of U.S. Ser. No. 08/472,802, filed Jun. 7, 1995, which is a continuation-in-part of 08/330,123, filed Oct. 27, 1994, now U.S. Pat. No. 5,583,016, which is a continuation-in-part of 08/272,102, filed Jul. 7, 1994 (abandoned), all of which are incorporated herein by reference.

BACKGROUND OF THE INVENTION

The present invention relates to mammalian telomerase genes and transcriptional regulatory regions thereof. The invention provides methods, cell lines, transgenic animals, and compositions relating to the fields of molecular biology, chemistry, pharmacology, and medical and diagnostic technology.

Telomerase is a ribonucleoprotein enzyme that synthesizes one strand of the telomeric DNA using as a template a sequence contained within the RNA component of the enzyme. See Blackburn (1992) *Annu. Rev. Biochem.* 61:113–129. Mammalian telomerase is composed of one or more protein components and an RNA component. The RNA component comprises a template repeat sequence complementary to the telomere repeat sequence. The RNA component of human telomerase ("HTR") has been reported (Feng et al. (1995) *Science* 269:1267, and the PCT publication Nos. 95/13381, published 18 May 1995; 95/13382, published 18 May 1995; 93/23572, published Nov. 25, 1993; and 96/01835, published 25 Jan., 1995 (incorporated herein in their entirety)).

Telomeres have an important biological role in maintaining chromosome structure and function. Current evidence is consistent with the idea that a loss of telomeric DNA acts as a trigger of cellular senescence and aging and that regulation of telomerase has important biological implications (see Harley (1991) *Mutation Research* 256:271). Telomerase activity has also been correlated with neoplastic transformation and cancer, wherein cancer cells characteristically exhibit telomerase activity. Most cancer cells or immortalized cell lines express high levels of telomerase activity, while in most normal somatic human cells, telomerase is not detected (Kim et al. (1994) *Science* 266:2011). Expression of antisense RNA complementary to hTR in an immortal human cancer cell line (HeLa) has been shown to induce cell crisis and cell death after a number of cell doublings (PCT patent publication No. 96/01835, published 25 Jan., 1996).

The transcriptional regulation of telomerase genes and factors or agents which can influence the expression of telomerase genes are not well-defined in the art. The development of transcriptional regulators which would afford a basis to control the expression of specific genes, such as telomerase genes, is a desired goal. Such transcriptional regulators can be pharmaceuticals for treating or preventing telomerase-related pathological conditions.

There is a great need in the art for methods and systems for identifying agents which regulate expression of mammalian telomerase. Significant improvements to and new opportunities for telomerase-mediated therapies and drug development methods could be realized if methods and systems for evaluating transcriptional effects of agents on expression of genes encoding the RNA component and/or encoding the protein components of telomerase were available.

The present invention meets these and other needs and provides such improvements and opportunities. The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

In a first aspect, the present invention provides a telomerase reporter construct comprising a transcription regulatory region of a mammalian telomerase gene operably linked to a reporter polynucleotide. The construct is useful in reporting transcriptional activity of a mammalian telomerase gene transcription regulatory region.

The transcription regulatory region comprises a promoter, generally the native promoter(s) associated with the naturally occurring mammalian telomerase gene, in particular, a telomerase RNA component gene. The regions typically further comprise a transcription factor recognition site(s) located within about 20 kilobases of a promoter in the naturally-occurring telomerase gene in the mammalian genome. Often, a transcription regulatory region comprises a substantially contiguous segment of DNA spanning from about 10 kilobases upstream, typically 5 kilobases or less upstream, of the transcription start site and continuing downstream to or through the transcription start site.

In one embodiment, the transcription regulatory region comprises sequences from the hTR promoter region including, e.g., about 1.4 kb upstream of nucleotide 1459 of SEQ ID NO:1, for example, nucleotides 1–1458 of SEQ ID NO:1 or nucleotides between about 1200 and 1458 of SEQ ID NO:1. Often, the transcription regulatory region of the telomerase gene is a predetermined cis-acting mammalian telomerase transcription regulatory sequence that comprises a predetermined polynucleotide sequence, such as an identified promoter sequence, a TATA box, a CCAAT box, a recognition site sequence for AP-1, AP-2, Sp1, NFAT, OCT-1, OCT-2, OAP, NFκB, CREB, CTF, TFIIA, TFIIB, TFIID, Pit-1, C/EBP, SRF, or other transcription factor having a known binding site sequence, or the like. The hTR promoter may contain a mix of pol II and pol III promoter elements, or may contain totally novel regulatory elements. Typically, the predetermined cis-acting mammalian telomerase transcription regulatory region comprises subregions which are identifiable by foot-printing patterns produced by proteins present in a nuclear extract of mammalian cells expressing said telomerase gene and/or in cells in which said telomerase gene is substantially not transcribed.

The reporter polynucleotide sequence is heterologous to the transcription regulatory region. That is, the reporter polynucleotide sequence is not found operably linked with the transcription regulatory sequence in nature. The reporter polynucleotide sequence can comprise a selectable marker gene (e.g., neo, HPRT, screenable cell surface protein, auxotrophic gene), a detectable gene product (e.g., luciferase, fluorescent protein, β-galactosidase, a cell surface protein, a hybridizable transcript having a predetermined sequence complementary to a probe or primer), or the like. A reporter polynucleotide is suitable if its transcription provides a basis for reporting transcription driven by a cis-linked sequence, and, for certain embodiments, preferably also for identifying and selecting cells in which the reporter polynucleotide sequence is substantially transcribed.

The telomerase reporter construct can include additional polynucleotide sequences, such as: origins of replication for prokaryotic and/or eukaryotic host cells, sequences for gene targeting or targeted integration by homologous recombination, polyadenylation sequences, splicing sequences, heterologous promoters, predetermined sequence elements, and the like. The telomerase reporter constructs of this invention are recombinant nucleic acid molecules.

In a second aspect, the invention provides methods for determining whether an agent modulates expression from a telomerase reporter construct. Expression includes expression, processing, assembly or stability of the reporter polynucleotide sequence.

In one embodiment, the method typically comprises determining whether the agent modulates transcription of the reporter polynucleotide sequence of said telomerase reporter construct in a transcription assay, which is generally: (1) an in vitro transcription reaction having a telomerase reporter construct, (2) a stably or transiently transfected host cell having a telomerase reporter construct, or (3) a transgenic animal having a genome having a telomerase reporter construct; wherein modulation is defined as a reproducible and detectable increase or decrease in expression of the reporter polynucleotide sequence in the presence of said agent as compared to a comparable transcription assay lacking said agent.

In one embodiment, the agent is introduced into or administered to a transcription assay wherein sequence-specific transcriptional regulation of a reporter gene is effected by a predetermined cis-acting operably linked mammalian telomerase transcription regulatory region.

In a third aspect, the invention provides a host cell comprising a telomerase reporter construct. The telomerase reporter construct can be present as a recombinant polynucleotide sequence in the genome of the cell (e.g., homologously integrated into a predetermined chromosomal locus or non-homologously integrated), can be present as a replicable episome (e.g., as a plasmid, viral genome, or artificial chromosome), or can be present as a non-replicable episome, such as for transient expression assays. In an aspect, the host cell is a eukaryotic cell, for example a yeast cell, an insect cell, or a mammalian cell. In an aspect, the host cell is a mammalian cell that expresses the endogenous, naturally-occurring telomerase gene, and may express detectable telomerase activity. In an aspect, the host cell is a mammalian cell that substantially does not transcribe the endogenous, naturally-occurring telomerase gene, and substantially lacks detectable telomerase activity. In a preferred aspect, the host cell is a human cell.

In a fourth aspect, the invention provides a transgenic non-human animal comprising a genomic copy of a telomerase reporter construct. In a variation, the telomerase reporter construct is present in the genome of the animal as a germline copy, or multiple copies, which are non-homologously integrated into one or more chromosomal locus. In a variation, the telomerase reporter construct is present in the genome of the animal as a germline copy, or multiple copies, which are homologously integrated into a chromosomal locus. In a variation, the telomerase reporter construct is present in the genome of a subset of somatic cells in the animal and is substantially not present in germ cells. In a variation, the telomerase reporter construct is present in the genome of cells of one organ, tissue, or cell type of the animal and is substantially absent in other cells of the animal.

In a fifth aspect, the invention provides a method for generating cells wherein chromatin position conditionally represses expression of a reporter polynucleotide that is integrated or homologously recombined into a chromosomal locus.

In a variation of this method, a reporter polynucleotide comprises a polynucleotide sequence encoding a selectable drug marker gene (e.g., neo, HPRT, etc.) under transcriptional control of an operably linked transcription regulatory region which comprises an hTR promoter or which typically is not derived from a mammalian telomerase gene and often is substantially constitutively active in a mammalian cell line (e.g., an SV40 large T Ag promoter/enhancer, GAPDH promoter, etc.). The reporter polynucleotide is introduced into a cell population, such as a cultured cell line or organism, and the cell population is cultured in the presence of an agent predetermined to reduce position effect (e.g., 0.5 mM sodium butyrate) and the cell population is exposed to a positive selection agent (e.g., G-418 for $neo^R$; HAT medium for positive selection of HPRT-expressing cells; gancyclovir for tk-expressing cells, and the like) and the population is selected for cells expressing the presence of the drug marker. The selected population is cultured in the substantial absence of said agent predetermined to reduce position effect, and the cell population is exposed to a negative selection agent (e.g., FIAU for tk-expressing cells, 6-thioguanine for HPRT-expressing cells) which selects for cells which substantially lack expression of the drug marker. The resultant cell doubly-selected subpopulation is enriched in cells which have integrated reporter polynucleotides exhibiting position effect, wherein the reporter polynucleotide is expressed under conditions where position effect is relieved (e.g., 0.5 mM sodium butyrate), but is substantially transcriptionally repressed by position effect in the absence of agents which relieve position effect. The doubly-selected cell population typically comprises a collection of cell clones which have integrated reporter polynucleotides into position effect-sensitive chromatin regions; these cells are termed "position effect reporter cells." In a variation, individual clonal progeny of position effect reporter cells are selected from the doubly-selected cell population for subsequent use.

In a sixth aspect, the invention provides a method for identifying agents which modulate chromatin position effects on expression of a reporter polynucleotide that is integrated or homologously recombined into a chromosomal locus. Position effect reporter cells are cultured in conditions wherein the integrated reporter polynucleotide is substantially transcriptionally silent, the cells are exposed to an agent, and transcription of the reporter polynucleotide is determined (e.g., by positive selection, negative selection, RNA transcript analysis, or other phenotypic determination or assay). An agent which produces a detectable increase in transcription of the reporter polynucleotide as compared to the position effect reporter cells cultured in the absence of the agent is thereby identified as a position effect modulatory agent, and more specifically as position effect antagonists. In a variation, position effect cells are cultured under conditions where position effect is relieved (e.g., 0.5 mM sodium butyrate), the cells are exposed to an agent, and transcription of the reporter polynucleotide is determined (e.g., by positive selection, negative selection, RNA transcript analysis, or other phenotypic determination or assay). An agent which produces a detectable decrease in transcription of the reporter polynucleotide as compared to the position effect reporter cells cultured in the absence of the agent is thereby identified as a position effect modulatory agent, and more specifically as position effect agonists.

In a variation of the sixth aspect, a cDNA expression library is introduced into a population of position effect reporter cells, whereby a library of position effect reporter cells is created wherein the position effect reporter cells individually express cDNA library members, which can be in either sense or antisense orientation, or a combination of sense and antisense orientations. In this embodiment, the introduced cDNA expression library member can serve as the agent and expressed cDNA library members which produce a detectable decrease or increase in reporter polynucleotide transcription as compared to cells lacking a cDNA library member are thereby identified as position effect antagonists or agonists, respectively. In a variation, a predetermined position effect modulator is added to a telomerase assay and the effect on telomerase activity is determined. In a variation, a predetermined position effect modulator is administered to a cell which does not express telomerase in the absence of the agent and the ability of the agent to induce detectable telomerase is determined. In a variation, a predetermined position effect modulator is administered to a telomerase-expressing cell and the ability of the agent to repress telomerase activity is determined.

In one embodiment, the agent is a polynucleotide, such as an antisense RNA transcribed from an antisense cDNA expression library member transfected into a position effect reporter cell.

In a seventh aspect, the invention provides methods for treating a condition associated with the telomerase activity within a cell or group of cells by contacting the cell(s) with a therapeutically effective amount of an agent that alters position effect of gene sequences in that cell. Such telomerase-modulating agents are often small molecules (e.g., less than about 3000 Daltons) and can be used to modify telomerase activity in vitro and in vivo, frequently for therapeutic effect, and are used as laboratory reagents and/or pharmaceuticals. In a related aspect, the invention provides pharmaceutical compositions comprising these therapeutic agents together with a pharmaceutically acceptable carrier or salt, which may include formulation in a lipofection complex, liposome, or immunoliposome for targeted delivery of the therapeutic agent. The invention also provides combinations of such telomerase-mediated therapeutic agents with other pharmaceuticals, such as antineoplastic agents and other cytotoxic or cytostatic agents; antifungal agents (e.g., for treatment of AIDS patients); nucleotides, nucleosides, and analogs thereof; and other pharmaceutical agents suitable for treating disease conditions such as neoplasia, hyperplasia, HIV-infection/AIDS and associated pathologies, and other diseases characterized by abnormal telomere metabolism.

In an eighth aspect, this invention provides therapeutic agents which inhibit neoplasia or apoptosis by modulating telomerase function by inhibiting or augmenting formation of telomerase RNA component or protein component by modulating transcription of one or more of the telomerase genes; such agents can be used as pharmaceuticals. Such pharmaceuticals will be used to treat a variety of human and veterinary diseases, such as: neoplasia, hyperplasia, neurodegenerative diseases, aging, AIDS, fungal infection, and the like.

In one embodiment, the invention provides methods for identifying, from a bank or library of agents, candidate telomerase gene transcription modulating agents which modulate telomerase gene transcription and/or transcription of gene that are under position effect influence of a telomere.

In another embodiment, candidate telomerase gene transcription modulating agents are identified by their ability to produce a statistically significant increase or decrease in transcription initiation rate and/or RNA transcript abundance of a reporter polynucleotide sequence operably linked to a mammalian telomerase transcription regulatory region of a telomerase protein component gene or a telomerase RNA component gene.

In another embodiment, candidate telomerase transcription modulating agents are identified by their ability to produce a statistically significant reduction or increase in transcription of a reporter polynucleotide sequence (e.g., β-galactosidase gene, luciferase gene, HPRT gene, etc.) operably linked to a transcriptional regulatory sequence of a mammalian telomerase RNA component gene, preferably a human telomerase RNA component gene, in a metabolically active mammalian cell. In a variation, an endogenous telomerase RNA component gene in a mammalian cell is targeted with a homologous targeting construct to place a reporter polynucleotide sequence in operable linkage to the upstream transcription regulatory sequence (e.g., promoter) of the endogenous telomerase RNA component gene in the chromosomal locus of the endogenous gene. In an alternative variation, an exogenous polynucleotide comprising a reporter polynucleotide is operably linked to a mammalian telomerase RNA component gene transcription regulatory region (e.g., promoter and upstream transcription factor binding sites); the exogenous polynucleotide is transferred into a mammalian cell wherein it may integrate non-homologously into a chromosomal location and/or is maintained or replicated as an episomal polynucleotide. Transcription of the reporter polynucleotide sequence can be determined by any suitable method, including but not limited to determining a phenotypic characteristic conferred on a cell by a protein encoded by the reporter polynucleotide sequence, detection by hybridization with a complementary probe polynucleotide, detection by PCR amplification, or the like. Agents which produce a statistically significant transcriptional modulation of the reporter polynucleotide in cells treated with the agent are thereby identified as candidate mammalian telomerase transcription modulating agents.

In a ninth aspect, the invention also provides chimeric alleles of mammalian telomerase RNA component genes, wherein a heterologous transcription regulatory region drives expression of an operably-linked mammalian telomerase RNA component gene to functionally express the telomerase RNA component gene under control of a heterologous promoter, which may be constitutive, inducible, tissue-specific, and/or derived from the same or different species of animal as the RNA component encoding gene. In an alternative embodiment, the chimeric gene comprises a telomerase gene transcription regulatory region that drives expression of an operably-linked reporter gene to functionally express the reporter gene under control of the telomerase gene promoter. Transgenic animals harboring a germline copy of a transgene comprising such chimeric genes can be made.

In a variation, a chimeric gene comprising a telomerase transcription regulatory region operably linked to a reporter gene is constructed by homologous gene targeting to operably link said reporter gene to the telomerase gene promoter in the telomerase gene locus. Transgenic animals of these types are used as commercial reagents for toxicology screening, for sale to pharmaceutical research laboratories to identify or investigate telomerase-modulating agents, as pets, and as agricultural livestock among other uses.

In a tenth aspect, this invention provides tagged RNA component constructs for determining whether an agent inhibits the association of a mammalian RNA component of telomerase with a protein component of telomerase. Constructs of this aspect of the invention comprise a transcription regulatory region operably linked to a nucleotide sequence comprising a sequence coding for the expression of a mammalian RNA component of telomerase and a tag sequence. The transcription regulatory region preferably is heterologous to the sequence encoding a mammalian RNA component of telomerase. For example, the region can comprise a constitutive promoter or inducible promoter and is, preferably a high expression promoter. The mammalian RNA component of telomerase can be hTR or the RNA component of any other mammal, such as a mouse, etc. The tag is a sequence that is capable of specific recognition by a binding substance. For example, the tag can be a sequence that is specifically recognized by an antibody. Also, the tag can code for the expression of the sequence of a DNA binding domain, such as the tar sequence which is recognizable by tat. The ability of the tag to be recognized allows one to isolate the entire transcript and any molecules bound to it, specifically, protein components of telomerase. The sequences encoding the tag can be placed either up-steam or down-stream of the sequence coding for the expression of the RNA component of telomerase. Upon expression the construct produces a tagged RNA component of telomerase.

In an eleventh aspect, this invention provides methods of determining whether an agent inhibits association between a mammalian RNA component of telomerase and a protein component of telomerase. The methods involve contacting a cell that expresses a tagged RNA component of telomerase and a protein component of telomerase with an agent, capturing the tagged RNA component of telomerase and determining whether the amount of protein bound to the tagged RNA component is different than the amount bound in the absence of the agent. A decreased amount of bound protein indicates that the agent inhibits the association of the RNA component of telomerase with a protein component of telomerase. One means of determining the amount of bound protein is by using immunoassays involving antibodies that recognize protein components of telomerase.

In a twelfth aspect, this invention provides methods of inhibiting the growth of a cell that expresses telomerase. Such methods are useful, for example, in the treatment of malignant cells that express telomerase, in sterilization by inhibiting the growth of germ cells or in eliminating telomerase-expressing cells from cell cultures. The methods involve transfecting the cell with an expression cassette comprising a transcription regulatory region of a mammalian telomerase gene operably linked to a nucleotide sequence coding for the expression of a product lethal to the cell. The expression cassette can be part of a vector used in gene therapy, such as an adenoviral or retroviral vector. The lethal product can be directly lethal or lethal after administration of a co-factor. Examples of genes encoding lethal products are ion channel toxins or gpt, which becomes lethal upon administration of 6-thio-Guanine. It may be useful to titrate the agent or modulate the general strength of the overall transcription unit to ensure that leaky expression from the transcription regulatory region does not kill normal cells.

DETAILED DESCRIPTION OF THE INVENTION

I. DEFINITIONS

Figure 1:
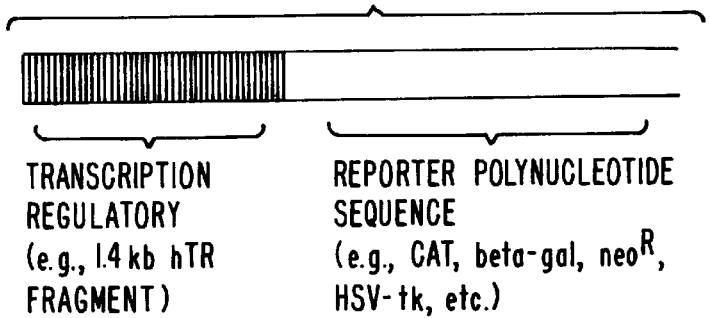
FIG. 1 shows schematically an example of a telomerase reporter construct exemplified as a reporter polynucleotide sequence operably linked to a transcription regulatory region of a mammalian telomerase gene in Panel (A), and with transcriptional elements and specific components of a particular construct in Panel (B).
Figure 1:
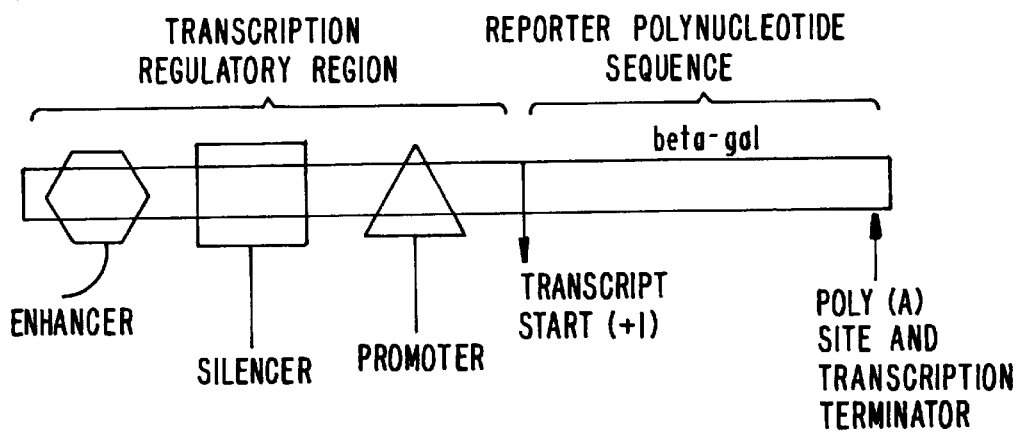

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms as used herein have the following meanings.

Unless specified otherwise, the left-hand end of a single-stranded polynucleotide sequence is the 5' end; the left-hand direction of a double-stranded polynucleotide sequence is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "cognate" refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

The term "recombinant nucleic acid molecule" refers to a nucleic acid molecule which is not naturally occurring, and which comprises two nucleotide sequences which are not naturally joined together. Recombinant nucleic acid molecules are produced by artificial recombination, e.g., genetic engineering techniques or chemical synthesis.

The term "agent" refers to a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as transcription modulatory agents (e.g., telomerase gene antagonists or agonists, antineoplastic agents, cytotoxic agents, cell proliferation-promoting agents, and the like) by inclusion in screening assays described herein or the like. Agents are evaluated for potential activity as specific telomerase gene transcription modulators (i.e., an agent which selectively modulates transcription of a telomerase gene but which does not substantially interfere with cell viability) by inclusion in screening assays described hereinbelow.

The term "corresponds to" is used herein to mean that a polynucleotide sequence is identical to all or a portion of a reference polynucleotide sequence. In contradistinction, the term "complementary to" is used herein to mean that one polynucleotide has the sequence of the binding partner of another polynucleotide. For illustration, the nucleotide sequence "5'-TATAC-3'" corresponds to a reference sequence "5'-TATAC-3'" and is complementary to a reference sequence "3'-GTATA-5'". Unless indicated otherwise, a specified sequence optionally describes the complementary sequence thereof.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80% sequence identity, preferably at least 85% identity and often 89% to 95% sequence identity, more usually at least 99% sequence identity as compared to a reference sequence over a comparison window of at least 20 nucleotide positions, optionally over a window of at least 30–50 nucleotides, wherein the percentage of sequence identity is calculated by comparing the reference sequence to the polynucleotide sequence that may include deletions or additions which total 20 percent or less of the reference sequence over the window of comparison. The reference sequence may be a subset of a larger sequence, for example, as a segment of the full-length telomerase RNA component nucleotide sequence.

The term "specific hybridization" refers to the formation, by hydrogen bonding or nucleotide (or nucleobase) bases, of hybrids between a probe polynucleotide (e.g., a polynucleotide of the invention and a specific target polynucleotide (e.g., a telomerase RNA component or genomic gene sequence)), wherein the probe preferentially hybridizes to the specific target such that, for example, a single band corresponding to, e.g., one or more of the RNA species of the telomerase RNA component gene (or specifically cleaved or processed telomerase RNA component species) can be identified on a Northern blot of RNA prepared from a suitable source (e.g., a somatic cell expressing telomerase RNA component). Such hybrids may be completely or only partially base-paired. Polynucleotides of the invention which specifically hybridize to mammalian telomerase RNA component or human telomeric sequences may be prepared on the basis of the sequence data provided herein and available in the patent applications incorporated herein and scientific and patent publications noted above, and according to methods and thermodynamic principles known in the art and described in Sambrook et al., *Molecular Cloning: A Laboratory Manual*, 2nd Ed., (1989), Cold Spring Harbor, N.Y.; Berger and Kimmel, *Methods in Enzymology*, Volume 152, Guide to Molecular Cloning Techniques (1987), Academic Press, Inc., San Diego, Calif.; and Goodspeed et al. (1989) *Gene* 76:1.

"Physiological conditions" refers to temperature, pH, ionic strength, viscosity, and like biochemical parameters that are compatible with a viable organism, and/or that typically exist intracellularly in a viable cultured mammalian cell, particularly conditions existing in the nucleus of said mammalian cell. For example, the intranuclear or cytoplasmic conditions in a mammalian cell grown under typical laboratory culture conditions are physiological conditions. Suitable in vitro reaction conditions for in vitro transcription cocktails are generally physiological conditions, and may be exemplified by a variety of art-known nuclear extracts. In general, in vitro physiological conditions can comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 0–250 mM NaCl, 5–50 mM Tris HCl, pH 5–8, with optional addition of divalent cation(s), metal chelators, nonionic detergents, membrane fractions, anti-foam agents, and/or scintillants.

The terms "label" or "labeled" refer to incorporation of a detectable marker, e.g., a radiolabeled nucleotide or amino acid, or a recoverable label (e.g. biotinyl moieties that can be recovered by avidin or streptavidin). Recoverable labels can include covalently linked polynucleobase sequences that can be recovered by hybridization to a complementary sequence polynucleotide. Various methods of labeling polypeptides and polynucleotides are known in the art and may be used. Examples of labels include, but are not limited to, the following: radioisotopes (e.g., $^3H$, $^{14}C$, $^{32}P$, $^{35}S$, $^{125}I$, $^{131}I$), fluorescent or phosphorescent labels (e.g., FITC, rhodamine, lanthanide phosphors, fluorescent proteins), enzymatic labels (e.g., horseradish peroxidase, β-galactosidase, luciferase, alkaline phosphatase), biotinyl groups, predetermined polypeptide epitopes recognized by a secondary reporter (e.g., digoxigenin, leucine zipper pair sequences, binding sites for antibodies, transcriptional activator polypeptide, metal binding domains, epitope tags). In some embodiments, labels are attached by spacer arms of various lengths, e.g., to reduce potential steric hindrance.

The term "statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

The term "anti-neoplastic agent" refers to agents that have the functional property of inhibiting the development or progression of a neoplasm in a mammal, e.g., a human, and may also refer to the inhibition of metastasis or metastatic potential.

The term "transcriptional modulation" refers to the capacity to either enhance transcription or inhibit transcription of a structural sequence or reporter sequence linked in cis; such enhancement or inhibition may be contingent on the occurrence of a specific event, such as stimulation with an inducer and/or may only be manifest in certain cell types. The altered ability to modulate transcriptional enhancement or inhibition may affect the inducible transcription of a gene, or may effect the basal level transcription of a gene, or both.

A "reporter polynucleotide" is a polynucleotide sequence which, when expressed, produces a RNA species and/or a phenotype which can be detected, screened for, and/or selected for. Preferably, a detection assay can quantitate the relative level of expression of a reporter polynucleotide. For example, a reporter polynucleotide may comprise an inducible or constitutive enhancer-promoter directing transcription of a sequence encoding a reporter protein (e.g., luciferase, β-galactosidase, chloramphenicol acetyltransferase, HPRT, fluorescent protein, thymidine kinase, neoR, and the like). Such a reporter polynucleotide may be transferred to a responsive or competent cell line for use as a reporter host cell to screen a panel of agents for the ability to produce transcriptional modulation. Agents that enhance transcription of the cis-linked reporter gene are identified as putative positive regulators of transcription. Numerous other specific examples of transcription regulatory elements, such as specific enhancers and silencers, are known to those of skill in the art and may be selected for use in the methods and polynucleotide constructs of the invention on the basis of the practitioner's desired application. Literature sources and published patent documents, as well as GenBank™ and other sequence information data sources can be consulted by those of skill in the art in selecting suitable transcription regulatory elements for use in the invention. Where necessary, a transcription regulatory element may be constructed by synthesis (and ligation, if necessary) of oligonucleotides made on the basis of available sequence information (e.g., GenBank sequences for a CD4 enhancer or a SV40 early promoter). The altered ability to modulate transcriptional enhancement or inhibition may affect the inducible transcription of a gene, the basal level transcription of a gene, or both. Agents that disrupt, for example, binding of silencer proteins to silencer transcription regulatory elements typically produce an increase in basal and/or induced transcription rate of a cis-linked gene.

The term "transcriptional enhancement" refers to the functional property of producing an increase in the rate of transcription of linked sequences that contain a functional promoter.

The term "transcription regulatory region" refers to a DNA sequence comprising a functional promoter and any associated transcription elements (e.g., enhancer, CCAAT box, TATA box, SPI site, etc.) that are essential for transcription of a polynucleotide sequence that is operably linked to the transcription regulatory region.

The term "transcriptional regulatory element" refers to a DNA sequence which activates transcription alone or in combination with one or more other DNA sequences. A transcriptional regulatory element can, for example, comprise a promoter and/or enhancer.

The terms "transcription factor recognition site" and "transcription factor binding site" refer to a polynucleotide sequence(s) or sequence motif(s) which is identified as being a site for the sequence-specific interaction of one or more transcription factors, frequently taking the form of direct protein-DNA binding. Typically, transcription factor binding sites can be identified by DNA foot-printing, gel mobility shift assays, and the like, and/or can be predicted on the basis of known consensus sequence motifs, or by other methods known to those of skill in the art. For example and not to limit the invention, eukaryotic transcription factors include, but are not limited to: NFAT, AP1, AP-2, Sp1, OCT-1, OCT-2, OAP, NFκB, CREB, CTF, TFIIA, TFIIB, TFIID, Pit-1, C/EBP, SRF (Mitchell P. J. and Tijan R. (1989) *Science* 245: 371). For purposes of the invention, steroid receptors, RNA polymerases and associated factors, and other proteins that interact with DNA in a sequence-specific manner and exert transcriptional regulatory effects are considered transcription factors.

The terms "transcriptional unit" and "transcriptional complex" refer to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

The term "telomerase RNA component gene" refers to a polynucleotide which is a naturally-occurring mammalian gene encoding the RNA component of telomerase, typically a primate telomerase RNA component such as a human or monkey telomerase RNA component or the cognate gene in heterologous species (e.g., mouse or rat). Some telomerase RNA component alleles have sequence variations as compared to known naturally-occurring telomerase RNA component genes. A preferred RNA component is a full length mature human telomerase RNA component (hTR) (see SEQ ID NO:2; Feng et al. (1995) *Science* 269: 1267; PCT patent publication Nos. 95/13381, published 18 May 1995; 95/13382, published 18 May 1995; 93/23572, published Nov. 25, 1993; 96/01835, published 25 Jan., 1996; 96/01614, published 25 Jan., 1996; and commonly-assigned U.S. Ser. Nos. 08/521,634 filed 31 Aug., 1995; 08/330,123 filed 27 Oct., 1994; 08/472,802 filed 7 Jun., 1995; 08/482, 115 filed 7 Jun., 1995, and PCT/US95/08530 filed 6 Jul., 1995).

The term "hTR gene promoter region" refers to sequences encoding transcription regulatory elements located upstream of the hTR gene, i.e., upstream of nucleotide 1459 of SEQ ID NO:1, e.g., within about 1.4 kb of the hTR gene, such as nucleotides 1–1458 of SEQ ID NO:1.

The term "telomerase-dependent gene" refers to genes which manifest an altered rate of transcription, either increased or decreased, from a major or minor transcriptional start site for said gene, wherein such alteration in transcriptional rate correlates with the expression of a telomerase gene (e.g., hTR) gene).

The term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "reporter expression cassette" refers to a polynucleotide comprising a promoter sequence and, optionally, an enhancer and/or silencer element(s), operably linked to a structural sequence, such as a cDNA sequence or genomic DNA sequence encoding a reporter protein (e.g., luciferase, β-galactosidase, chloramphenicol acetyltransferase), such that the reporter gene sequence is under the transcriptional influence of a cis-acting transcription factor binding site and/or recognition site. In some embodiments, an expression cassette may also include polyadenylation site sequences to ensure polyadenylation of transcripts. When a reporter expression cassette is transferred into a suitable host cell, the structural sequence is transcribed from the expression cassette promoter, and a translatable message is usually generated, either directly or following appropriate RNA splicing.

The term "reporter host cell" refers to a eukaryotic cell, preferably a mammalian cell, which harbors a reporter expression cassette. Preferably, the reporter expression cassette polynucleotide is stably integrated into a host cell chromosomal location, either by non-homologous integration or by homologous sequence targeting, although transient transfection methods may be employed.

The term "endogenous DNA sequence" refers to naturally-occurring polynucleotide sequences contained in a eukaryotic cell. Such sequences include, for example, chromosomal sequences (e.g., structural genes, promoters, enhancers, recombinatorial hotspots, repeat sequences, integrated proviral sequences). A "predetermined sequence" is a sequence which may be selected at the discretion of the practitioner on the basis of known or predicted sequence information. An exogenous polynucleotide is a polynucleotide which is transferred into a eukaryotic cell.

The term "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (less than 3000 Daltons), and elemental ion species are not considered macromolecular species.

II. DESCRIPTION OF THE PREFERRED EMBODIMENTS

The present invention provides methods, reagents, genetically modified animals and cells, and pharmaceutical compositions relating to the ribonucleoprotein human telomerase. Preferably, the telomerase is of mammalian origin; human telomerase is especially preferred.

The nomenclature used hereafter and the laboratory procedures in cell culture, molecular genetics, and nucleic acid chemistry and hybridization described herein often involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al., *Molecular Cloning: A Laboratory Manual*, 2d ed. (1989) Cold Spring Harbor Laboratory Press, Cold Spring Harbor, N.Y.).

Oligonucleotides can be synthesized on an Applied BioSystems or other commercially available oligonucleotide synthesizer according to specifications provided by the manufacturer.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987).

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989).

A. Overview

Figure 2:
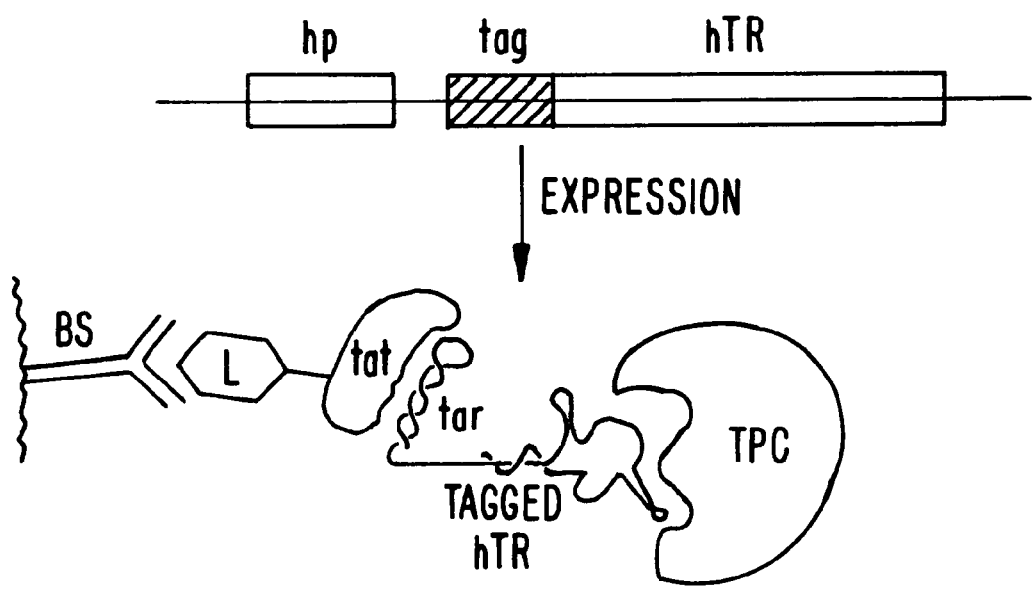
FIG. 2 shows a method of this invention for determining whether an agent inhibits binding of a mammalian RNA component of telomerase from binding with a protein component of telomerase. In the embodiment shown, a tagged RNA component construct contains a heterologous promoter ("hp") operably linked with a sequence encoding a tag ("tag") and a sequence coding for the expression of hTR ("hTR"). Expression of this sequence provides a tagged hTR polynucleotide. The cell expresses both the tagged hTR polynucleotide and telomerase protein component ("TPC"). The tagged hTR associates with TPC. Agents are tested for the ability to inhibit this association. The tagged construct and any associated TPC is isolated by, e.g., affinity methods. In the embodiment shown, the tag includes a tar sequence. The affinity reagent includes a tat moiety that binds to tar and an attached ligand ("L"). The complex is isolated using a binding substance ("BS") that recognizes the ligand.
Figure 3:
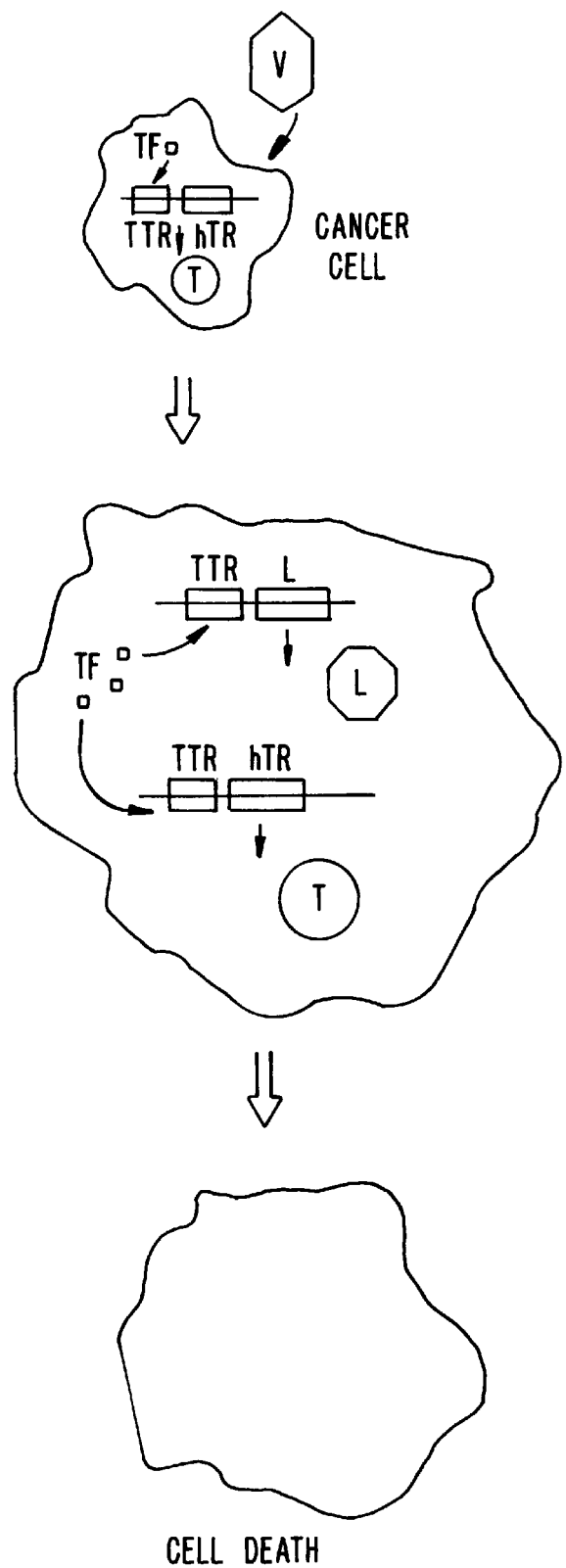
FIG. 3 shows a method of this invention for inhibiting growth (in this case killing) cells that express telomerase. A cancer cell contains transcription factors ("TF") that activate telomerase transcription regulatory elements ("TTR") that result in expression of human RNA component of telomerase ("hTR") that assembles into telomerase ("T"). Exposure to a vector ("V") transfects the cell with an expression cassette that includes a TTR operably linked to a lethal gene ("L"). The transcription factors activate transcription from the TTR to cause expression of the lethal gene product, which kills the cell.

The invention relates to methods and compositions for identifying agents which modulate transcription, and more particularly which modulate transcription position effect and/or telomerase gene expression. FIG. 2 illustrates schematically one embodiment of such a method and composition in which an agent is assayed for its ability to modulate the association between a tagged hTR construct and a protein component of telomerase.

B. Human Telomerase RNA Component Gene And Telomerase Gene Transcriptional Regulatory Elements A lambda clone designated 28-1 contains an ~15 kb insert containing human telomerase RNA component gene sequences. Clone 28-1 was deposited with the American Type Culture Collection pursuant to the Budapest Treaty and granted accession number ATCC 75925. An ~2.4 kb SauIIIA1-HindIII fragment containing the hTR sequences as well as transcription regulatory sequences of the ~15 kb insert was sequenced. The sequence is presented below as SEQ ID NO:1:

SEQ ID NO:1)

```
                                            50
GATCAGTTAGAAAGTTACTAGTCCACATATAAAGTGCCAAGTCTTGTACT

100
CAAGATTATAAGCAATAGGAATTTAAAAAAAGAAATTATGAAAACTGACA

150
AGATTTAGTGCCTACTTAGATATGAAGGGGAAAGAAGGGTTTGAGATAAT

200
GTGGGATGCTAAGAGAATGGTGGTAGTGTTGACATATAACTCAAAGCATT

250
TAGCATCTACTCTATGTAAGGTACTGTGCTAAGTGCAATAGTGCTAAAAA

300
CAGGAGTCAGATTCTGTCCGTAAAAAACTTTACAACCTGGCAGATGCTAT

350
GAAAGAAAAAGGGGATGGGAGAGAGAGAAGGAGGGAGAGAGATGGAGAGG

400
GAGATATTTTACTTTTCTTTCAGATCGAGGACCGACAGCGACAACTCCAC

450
GGAGTTTATCTAACTGAATACGAGTAAAACTTTTAAGATCATCCTGTCAT

500
TTATATGTAAAACTGCACTATACTGGCCATTATAAAAATTCGCGGCCGGG

550
TGCGGTGGCTCATACCTGTAATCCCAGCACTTTGGGAGGCCGAAGCGGGT

600
GGATCACTTGAGCCCTGGCGTTCGAGACCAGCCTGGGCAACATGGTGAAA

650
CCCCCGTCTCTACTAAAAACACAAAAACTAGCTGGGCGTGGTGGCAGGCG

700
CCTGTAATCCCAGCTACTCAGGAGGCTGAGACACGAGAATCGCTTGAACC

750
CGGGAGCAGAGGTTGCAGTGAGCCGAGATCACGCCACTAGACTCCATCCA

800
GCCTGGGCGAAAGAGCAAGACTCCGTCTCAAAAAAAAAAATCGTTACAAT

850
TTATGGTGGATTACTCCCCTCTTTTTACCTCATCAAGACACAGCACTACT

900
TTAAAGCAAAGTCAATGATTGAAACGCCTTTCTTTCCTAATAAAAGGGAG

950
ATTCAGTCCTTAAGATTAATAATGTAGTAGTTACACTTGATTAAAGCCAT

1000
CCTCTGCTCAAGGAGAGGCTGGAGAAGGCATTCTAAGGAGAAGGGGCAG

1050
GGTAGGAACTCGGACGCATCCCACTGAGCCGAGACAAGATTCTGCTGTAG

1100
TCAGTGCTGCCTGGGAATCTATTTTCACAAAGTTCTCCAAAAAATGTGAT

1150
GATCAAAACTAGGAATTAGTGTTCTGTGTCTTAGGCCCTAAAATCTTCCT

1200
GTGAATTCCATTTTTAAGGTAGTCGAGGTGAACCGCGTCTGGTCTGCAGA

1250
GGATAGAAAAAAGGCCCTCTGATACCTCAAGTTAGTTTCACCTTTAAAGA

1300
AGGTCGGAAGTAAAGACGCAAAGCCTTTCCCGGACGTGCGGAAGGGCAAC

1350
GTCCTTCCTCATGGCCGGAAATGGAACTTTAATTTCCCGTTCCCCCCAAC
```

```
                                               1400
CAGCCCGCCCGAGAGAGTGACTCTCACGAGAGCCGCGAGAGTCAGCTTGG

1450
CCAATCCGTGCGGTCGGCGGCCGCTCCCTTTATAAGCCGACTCGCCCGGC

1500
AGCGCACCGGGTTGCGGAGGGTGGGCCTGGGAGGGGTGGTGGCCATTTTT

1550
TGTCTAACCCTAACTGAGAAGGGCGTAGGCGCCGTGCTTTTGCTCCCCGC

1600
GCGCTGTTTTTCTCGCTGACTTTCAGCGGGCGGAAAAGCCTCGGCCTGCC

1650
GCCTTCCACCGTTCATTCTAGAGCAAACAAAAAATGTCAGCTGCTGGCCC

1700
GTTCGCCCCTCCCGGGGACCTGCGGCGGGTCGCCTGCCCAGCCCCCGAAC

1750
CCCGCCTGGAGGCCGCGGTCGGCCCGGGGCTTCTCCGGAGGCACCCACTG

1800
CCACCGCGAAGAGTTGGGCTCTGTCAGCCGCGGGTCTCTCGGGGCGAGG

1850
GCGAGGTTCAGGCCTTTCAGGCCGCAGGAAGAGGAACGGAGCGAGTCCCC

1900
GCGCGCGGCGCGATTCCCTGAGCTGTGGGACGTGCACCCAGGACTCGGCT

1950
CACACATGCAGTTCGCTTTCCTGTTGGTGGGGGAACGCCGATCGTGCGC

2000
ATCCGTCACCCCTCGCCGGCAGTGGGGGCTTGTGAACCCCCAAACCTGAC

2050
TGACTGGGCCAGTGTGCTGCAAATTGGCAGGAGACGTGAAGGCACCTCCA

2100
AAGTCGGCCAAAATGAATGGGCAGTGAGCCGGGGTTGCCTGGAGCCGTTC

2150
CTGCGTGGGTTCTCCCGTCTTCCGCTTTTTGTTGCCTTTTATGGTTGTAT

2200
TACAACTTAGTTCCTGCTCTGCAGATTTTGTTGAGGTTTTTGCTTCTCCC

2250
AAGGTAGATCTCGACCAGTCCCTCAACGGGGTGTGGGGAGAACAGTCATT

2300
TTTTTTTGAGAGATCATTTAACATTTAATGAATATTTAATTAGAAGATCT

2350
AAATGAACATTGGAAATTGTGTTCCTTTAATGGTCATCGGTTTATGCCAG

2400
AGGTTAGAAGTTTCTTTTTTGAAAAATTAGACCTTGGCGATGACCTTGAG

2426
CAGTAGGATATAACCCCCACAAGCTT
```

The RNA component sequence begins at base 1459. A variety of transcriptional control elements can also be identified in the sequence. An A/T Box consensus sequence is found at nucleotides 1438–1444, PSE consensus sequences are found at nucleotides 1238–1259 as well as nucleotides 1406–1414, a CAAT box consensus sequence is found at nucleotides 1399–1406; an SPI consensus sequence is found at nucleotides 1354–1359 and a β-interferon response element consensus sequence is found at nucleotides 1234–1245.

Plasmid pGRN33 contains an ~2.5 kb HindIII-SacI insert containing sequences from lambda clone 28-1 that contain the sequence of hTR. Plasmid pGRN33 was deposited with the American Type Culture Collection pursuant to the Budapest Treaty and granted accession number ATCC 75926. A PstI fragment of the ~2.4 kb SauIIIA1--HindIII fragment of clone 28-1 also contains the hTR sequence. The sequence of the PstI fragment, determined upon re-sequencing, is provided in SEQ ID NO:2, below:

```
  1 CTGCAGAGGATAGAAAAAAGGCCCTCTGATACCTCAAGTTAGTTTCACCTTTAAAGAAGG   (SEQ ID NO:2)
    GACGTCTCCTATCTTTTTTCCGGGAGACTATGGAGTTCAATCAAAGTGGAAATTTCTTCC
    -PST1-

61 TCGGAAGTAAAGACGCAAAGCCTTTCCCGGACGTGCGGAAGGGCAACGTCCTTCCTCATG
    AGCCTTCATTTCTGCGTTTCGGAAAGGGCCTGCACGCCTTCCCGTTGCAGGAAGGAGTAC

121 GCCGGAAATGGAACTTTAATTTCCCGTTCCCCCCAACCAGCCCGCCCGAGAGAGTGACTC
    CGGCCTTTACCTTGAAATTAAAGGGCAAGGGGGGTTGGTCGGGCGGGCTCTCTCACTGAG

181 TCACGAGAGCCGCGAGAGTCAGCTTGGCCAATCCGTGCGGTCGGCGGCCGCTCCCTTTAT
    AGTGCTCTCGGCGCTCTCAGTCGAACCGGTTAGGCACGCCAGCCGCCGGCGAGGGAAATA

*********************************
241 AAGCCGACTCGCCCGGCAGCGCACCGGGTTGCGGAGGGTGGGCCTGGGAGGGGTGGTGGC
    TTCGGCTGAGCGGGCCGTCGCGTGGCCCAACGCCTCCCACCCGGACCCTCCCCACCACCG

***************************************************
301 CATTTTTTGTCTAACCCTAACTGAGAAGGGCGTAGGCGCCGTGCTTTTGCTCCCCGCGCG
    GTAAAAAACAGATTGGGATTGACTCTTCCCGCATCCGCGGCACGAAAACGAGGGGCGCGC

***************************************************
361 CTGTTTTTCTCGCTGACTTTCAGCGGGCGGAAAAGCCTCGGCCTGCCGCCTTCCACCGTT
    GACAAAAAGAGCGACTGAAAGTCGCCCGCCTTTTCGGAGCCGGACGGCGGAAGGTGGCAA

***************************************************
421 CATTCTAGAGCAAACAAAAAATGTCAGCTGCTGGCCCGTTCGCCCCTCCCGGGGACCTGC
    GTAAGATCTCGTTTGTTTTTTACAGTCGACGACCGGGCAAGCGGGGAGGGCCCCTGGACG hTR
          ***************************************************
481 GGCGGGTCGCCTGCCCAGCCCCCGAACCCCGCCTGGAGGCCGCGGTCGGCCCGGGGCTTC
    CCGCCCAGCGGACGGGTCGGGGGCTTGGGCGGACCTCCGGCGCCAGCCGGGCCCCGAAG

***************************************************
541 TCCGGAGGCACCCACTGCCACCGCGAAGAGTTGGGCTCTGTCAGCCGCGGGTCTCTCGGG
    AGGCCTCCGTGGGTGACGGTGGCGCTTCTCAACCCGAGACAGTCGGCGCCCAGAGAGCCC

***************************************************
601 GGCGAGGGCGAGGTTCAGGCCTTTCAGGCCGCAGGAAGAGGAACGGAGCGAGTCCCCGCG
    CCGCTCCCGCTCCAAGTCCGGAAAGTCCGGCGTCCTTCTCCTTGCCTCGCTCAGGGGCGC

*****************************************************>
661 CGCGGCGCGATTCCCTGAGCTGTGGGACGTGCACCCAGGACTCGGCTCACACATGCAGTT
    GCGCCGCGCTAAGGGACTCGACACCCTGCACGTGGGTCCTGAGCCGAGTGTGTACGTCAA

721 CGCTTTCCTGTTGGTGGGGGGAACGCCGATCGTGCGCATCCGTCACCCCTCGCCGGCAGT
    GCGAAAGGACAACCACCCCCCTTGCGGCTAGCACGCGTAGGCAGTGGGGAGCGGCCGTCA

781 GGGGGCTTGTGAACCCCCAAACCTGACTGACTGGGCCAGTGTGCTGCAAATTGGCAGGAG
    CCCCCGAACACTTGGGGGTTTGGACTGACTGACCCGGTCACACGACGTTTAACCGTCCTC

841 ACGTGAAGGCACCTCCAAAGTCGGCCAAAATGAATGGGCAGTGAGCCGGGGTTGCCTGGA
    TGCACTTCCGTGGAGGTTTCAGCCGGTTTTACTTACCCGTCACTCGGCCCCAACGGACCT

901 GCCGTTCCTGCGTGGGTTCTCCCGTCTTCCGCTTTTTGTTGCCTTTTATGGTTGTATTAC
    CGGCAAGGACGCACCCAAGAGGGCAGAAGGCGAAAAACAACGGAAAATACCAACATAATG

961 AACTTAGTTCCTGCTCTGCAG
    TTGAATCAAGGACGAGACGTC
                 -PST1-
```

DNA sequences within or flanking a telomerase gene which is preferentially expressed in telomerase-expressing cells contain DNA sequence motifs which function to enhance or drive transcription of the cis-linked gene in cells. These sequences are termed telomerase gene transcriptional regulatory sequences. Such sequences are isolated and evaluated for their capacity to enhance or drive transcription of an operably linked reporter gene (e.g., CAT) in telomerase-expressing cells and substantially not in other cell types. Minimal functional sequences are defined by deletion analysis and/or linker-scanning mutagenesis and the like, followed by assay of transcriptional activity demonstrating transcription in transfected telomerase-expressing cells but not in other cell types which have also been transfected with minimal reporter constructs.

A telomerase gene transcriptional regulatory element can comprise a promoter and/or enhancer. For example, a telomerase gene enhancer is identified by deletion analysis of the upstream region between −10 kb and −0.01 kb, which typically can be isolated from the human genome as a restriction fragment. Such an enhancer is termed an "upstream telomerase enhancer." Optionally, the naturally-occurring telomerase promoter of the hTR gene can be included in operable linkage with the upstream enhancer. Alternatively, a heterologous promoter can be operably linked to the upstream enhancer and used to drive expression of an operably linked structural gene sequence (e.g., a toxin gene, reporter gene, or other encoding sequence). Various deletions and point mutations can be made to the upstream sequences of the hTR gene, and each variant evaluated for the ability to drive or enhance transcription of a reporter gene (e.g., CAT) in telomerase-expressing cells (e.g., HT1080 cells) and in cells substantially lacking telomerase expression (e.g., IMR90).

C. Transcriptional Regulatory Sequences

Transgenes and expression polynucleotides of the invention comprise a transcriptional regulatory sequence of a telomerase gene operably linked to a reporter gene or other structural gene and targeting constructs of the invention may comprise such a transcriptional regulatory sequence. Suitable transcriptional regulatory sequences are those which confer telomerase-specific transcription of the linked gene, although low levels of transcription may occur in cell which do not express telomerase so long as such leaky or background expression does not substantially interfere.

Suitable transcriptional regulatory sequences of the invention generally are derived from or correspond to polynucleotide sequences within or flanking a mammalian telomerase gene which is preferentially expressed in a telomerase-expressing cell population. For many intended purposes, the hTR gene is the preferred suitable source for obtaining telomerase-specific transcription regulatory sequences.

A reporter gene or other structural gene is preferably inserted in operable linkage with the hTR gene upstream enhancer (and optionally including the hTR promoter). The reporter gene (or other structural gene) is positioned to ensure correct transcription and translation according to standard cloning methods in the art. A targeting construct may be produced having recombinogenic homology regions flanking the reporter gene (or other structural gene) which correspond to the sequences flanking the chosen insertion site, which will be downstream of the transcription start site. A transgene comprising the regulatory sequences identified herein as the hTR transcription regulatory region can also be produced, however it may be desirable to include additional sequences upstream or downstream of the hTR transcription start site; such sequences can be readily isolated by routine "chromosome walking" screening of a human genomic library.

Expression of recombinant hTR in cells, particularly cells which are naturally telomerase negative, may be used to identify and isolate genes that are transcriptionally modulated, either positively or negatively, by the presence of hTR. Such genes are typically initially identified as cDNA clones isolated from subtractive cDNA libraries, wherein RNA isolated from cells expressing recombinant hTR and RNA isolated from control cells (i.e., not expressing recombinant hTR) are used to generate the subtractive libraries and screening probes. In such a manner, hTR-dependent genes may be isolated. hTR-dependent genes (or their regulatory sequences operably linked to a reporter gene) may be used as a component of an in vitro transcription assay; such transcription assays may be used to screen for agents which inhibit hTR-dependent gene transcription and are thereby identified as candidate telomerase modulatory agents.

In vitro transcription reactions are typically performed by conventional methods, wherein the transcription template is a reporter polynucleotide operably linked and under transcriptional control of a telomerase gene transcription regulatory region (e.g., the hTR gene promoter region). A modification of standard in vitro transcription cocktails is the use of a cell extract or nuclear extract from cells which express the telomerase gene (e.g., hTR gene). In an embodiment, the in vitro cocktail comprises labeled ribonucleotide triphosphates, a telomerase gene transcription template, a nuclear extract from HT1080 cells, and physiological conditions.

D. Reporter Gene Constructs

The polynucleotide sequence encoding a reporter protein is operably linked to cis-acting transcriptional regulatory sequences (e.g., promoter, enhancer) of a telomerase gene (e.g., hTR), so that the reporter protein is expressed in telomerase expressing cells in a manner similar to the expression of the endogenous hTR gene in naturally-occurring cells of the same or equivalent type, preferably neoplastic or immortal cells, stem cells, or germ cells. Thus, it is usually preferable to operably link a reporter sequence to transcriptional regulatory elements which naturally occur in or near the telomerase gene (e.g., hTR gene).

The operable linkage may be formed by homologous sequence targeting to place the reporter gene downstream of (i.e., towards the carboxy-terminus of the encoded naturally-occurring polypeptide in translational reading frame orientation) a transcriptional regulatory sequence (i.e., a promoter and the additional elements which confer specific cell-type expression) of the endogenous telomerase gene.

Alternatively, the operable linkage may be formed exogenously as a transgene, wherein the reporter gene is operably linked to a transcriptional regulatory sequence isolated from an endogenous telomerase gene, typically by genomic DNA cloning. In such transgenes, the transcriptional regulatory sequence is at least the minimal sequence(s) required for efficient cell-type specific expression, which generally is at least a promoter and at least about 0.2 kilobase (kb) upstream of the promoter, preferably at least about 1 to 3 kb upstream of the promoter, more preferably at least about 5 kb upstream of the promoter, and frequently at least about 8 kb or more upstream of the promoter. In the case of the hTR gene, at least a functional promoter and including about 1.4 kb upstream of the hTR gene confer telomerase-specific expression of operably linked structural gene (reporter gene) sequences. Frequently, sequences downstream of the promoter, especially intronic sequences, are included in the transgene constructs (Brinster et al. (1988) *Proc. Natl. Acad. Sci.* (U.S.A.) 85: 836. Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a transgene. Where convenient, it is preferred that a contiguous segment of genomic DNA sequence spanning the telomerase gene and containing as much upstream flanking sequence as convenient (typically about 1–10 kb) be used in the telomerase transcription reporter polynucleotide, transgene or targeting construct, with the reporter gene inserted so as to replace or displace at least the first intron of the gene and to be operably linked to the promoter(s). It is further recognized that a telomerase gene may comprise multiple promoters, which may individually be cell type-specific, and it is necessary to operably link the reporter gene to at least one promoter (or other transcriptional element) which confers transcription in telomerase expressing cells (especially neoplastic cells). Transcriptional elements which confer transcription in telomerase non-expressing cells and which are not necessary for efficient transcription in telomerase-expressing cells may be advantageously deleted from the telomerase transcription reporter polynucleotide, transgene or targeting construct to provide additional cell-type specificity.

If the transcription regulatory sequence(s) selected are relatively inefficient in transcribing the reporter gene, it may be desirable to incorporate multiple copies of a telomerase transcription reporter polynucleotide, transgene, or targeting construct to compensate with an enhanced gene dosage.

E. Telomerase reporter constructs

A telomerase reporter construct suitable for use in reporting transcriptional activity of a mammalian telomerase gene transcription regulatory region comprises a reporter polynucleotide sequence operably linked to a transcription regulatory region of a mammalian telomerase gene (e.g., hTR gene). The transcription regulatory region comprises a promoter, generally the native promoter(s) associated with the naturally occurring mammalian telomerase gene, and typically further comprises a transcription factor recognition site(s) located within about 20 kilobases of a promoter in the naturally-occurring telomerase gene in the mammalian genome. Often, a transcription regulatory region comprises a substantially contiguous segment of DNA spanning from at least about 10 kilobases upstream, typically 5 kilobases or less upstream, frequently at least 1.4 kb upstream, of the transcription start site and continuing downstream to or through the transcription start site.

The reporter polynucleotide sequence can comprise a selectable marker gene (e.g., neo, HPRT, screenable cell surface protein, auxotrophic gene), a detectable gene product (e.g., luciferase, fluorescent protein, β-galactosidase, a hybridizable transcript having a predetermined sequence complementary to a probe or primer), or the like. A reporter polynucleotide is suitable so long as its transcription provides a basis for reporting transcription, and, for certain embodiments, preferably also for identifying and selecting cells in which the reporter polynucleotide sequence is substantially transcribed.

The telomerase reporter construct can include additional polynucleotide sequences, such as: origins of replication for prokaryotic and/or eukaryotic host cells, sequences for gene targeting or targeted integration by homologous recombination, polyadenylation sequences, splicing sequences, heterologous promoters, predetermined sequence elements, and the like. In an embodiment, the telomerase reporter construct comprises the hTR gene promoter region comprising the hTR promoter and about 1.4 kb of immediate upstream sequences. Often, the transcription regulatory region of the telomerase gene is a predetermined cis-acting mammalian telomerase transcription regulatory sequence that comprises a predetermined polynucleotide sequence, such as an identified promoter sequence, a TATA box, a CCAAT box, a recognition site sequence for AP-1, AP-2, Sp1, NFAT, OCT-1, OCT-2, OAP, NFκB, CREB, CTF, TFIIA, TFIIB, TFIID, Pit-1, C/EBP, SRF, or other transcription factor having a known binding site sequence, or the like. Typically, the predetermined cis-acting mammalian telomerase transcription regulatory region comprises subregions which are identifiable by foot-printing patterns produced by proteins present in a nuclear extract of mammalian cells expressing said telomerase gene and/or in cells in which said telomerase gene is substantially not transcribed.

F. Methods for Identifying Telomerase Transcription Modulators

A method for identifying an agent which modulates transcription of a telomerase reporter construct typically comprises determining the ability of an agent, typically a predetermined agent, to modulate transcription of the reporter polynucleotide sequence of said telomerase reporter construct in a transcription assay, which is generally: (1) an in vitro transcription reaction having a telomerase reporter construct, (2) a stably or transiently transfected host cell having a telomerase reporter construct, or (3) a transgenic animal having a genome having a telomerase reporter construct; wherein modulation is defined as a reproducible and detectable increase or decrease in expression of the reporter polynucleotide sequence in the presence of said agent as compared to a comparable transcription assay lacking said agent. In an embodiment, an agent is introduced into or administered to a transcription assay wherein sequence-specific transcriptional regulation of a reporter gene is effected by a predetermined cis-acting operably linked mammalian telomerase transcription regulatory region.

G. Reporter Host Cells

A host cell comprising a telomerase reporter construct can be made from a variety of suitable cell types. The telomerase reporter construct can be present as a polynucleotide sequence in the genome of the cell (e.g., homologously integrated into a predetermined chromosomal locus or non-homologously integrated), can be present as a replicable episome (e.g., as a plasmid, viral genome, or artificial chromosome), or can be present as a non-replicable episome, such as for transient expression assays. In an aspect, the host cell is a eukaryotic cell, for example a yeast cell, an insect cell, or a mammalian cell. In an aspect, the host cell is a mammalian cell that expresses the endogenous, naturally-occurring telomerase gene, and may express detectable telomerase activity. In an aspect, the host cell is a mammalian cell that substantially does not transcribe the endogenous, naturally-occurring telomerase gene, and substantially lacks detectable telomerase activity. In an aspect, the host cell is a mammalian cell that detectably transcribes the endogenous, naturally-occurring telomerase gene, and has detectable telomerase activity. In a preferred aspect, the host cell is a human cell.

H. Transgenic Animals

Transgenic non-human animal comprising a genomic copy of a telomerase reporter construct can be made by those skilled in the art. In a variation, the telomerase reporter construct is present in the genome of the animal as a germline copy, or multiple copies, which are nor-homologously integrated into one or more chromosomal locus. In a variation, the telomerase reporter construct is present in the genome of the animal as a germline copy, or multiple copies, which are homologously integrated into a chromosomal locus. In a variation, the telomerase reporter construct is present in the genome of a subset of somatic cells the animal and is substantially not present in germ cells. In a variation, the telomerase reporter construct is present in the genome of cells of one organ, tissue, or cell type of the animal and is substantially absent in other cells of the animal.

Genomic clones of hTR, particularly of the murine or human hTR gene, may be used to construct homologous targeting constructs for generating cells and transgenic non-human animals having at least one functionally disrupted hTR allele. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534. Homologous targeting can be used to generate so-called "knockout" mice, which are heterozygous or homozygous for an inactivated hTR allele. Such mice may be sold commercially as research animals for investigation of immune system development, neoplasia, spermatogenesis, may be used as pets, may be used for animal protein (foodstuff), and other uses.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987). Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799).

I. Transgenes

Additionally, a hTR cDNA or genomic gene copy may be used to construct transgenes for expressing hTR at high levels and/or under the transcriptional control of transcription control sequences which do not naturally occur adjacent to the hTR gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a hTR polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods.

Alternatively, an hTR transcription regulatory region can be linked to a structural gene or a reporter polynucleotide to form a transgene which can be transferred into a cell, cell line, or non-human animal germline.

J. Therapeutic and Prophylactic Aspects

Because telomerase is active only in tumor, germline, and certain stem cells, for example stem cells of the hematopoietic system, other normal cells are not affected by telomerase inhibition therapy using telomerase transcription modulators of the present invention. Steps can also be taken to avoid contact of the telomerase inhibitor with germline or stem cells, although this may not be essential. For instance, because germline cells express telomerase activity, inhibition of telomerase may negatively impact spermatogenesis and sperm viability, and telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient, or more localized administration can be used.

These methods can be carried out by delivering to a patient, more particularly to diseased cells, a functional telomerase transcriptional modulator of the invention to the cell. For instance, the agent can be delivered in a liposome or other delivery enhancement formulation.

Telomerase transcriptional modulators can be used to derepress or inhibit telomerase activity in various human cells that otherwise lack detectable telomerase activity due to low levels of expression of the RNA component or a protein component of telomerase. If the telomerase RNA component is not sufficient to stimulate telomerase activity, then the agent can be introduced along with genes expressing the protein components of telomerase to stimulate telomerase activity. Thus, the invention provides methods for treating a condition associated with the telomerase activity within a cell or group of cells by contacting the cell(s) with a therapeutically effective amount of a telomerase transcription modulator that alters telomerase activity in that cell.

Cells that incorporate agents having the property of stimulating hTR gene expression from the promoter of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding the telomerase transcription modulator ex vivo to normal diploid cells include: telomere stabilization can arrest cellular senescence and allow potentially unlimited proliferative capacity of the cells; and normal diploid cells with an extended life span can be cultured in vitro for drug testing, virus manufacture, transplantation, or other useful purposes. In particular, ex vivo amplified stem cells of various types can be used in cell therapy for particular diseases, as noted above. Telomere stabilization can also suppress cancer incidence in replicating cells by preventing telomeres from becoming critically short as cells near crisis.

Cells that can be treated with telomerase gene transcription modulators that activate hTR transcription include but are not limited to hematopoietic stem cells (viral infections, including HIV infection leading to AIDS and post-chemotherapy), vascular endothelial cells (including cardiac and cerebral forms), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of a telomerase transcription modulator that functions to inhibit or stimulate telomerase activity under in vivo physiological conditions and is sufficiently stable under those conditions.

In related aspects, the invention features pharmaceutical compositions including a therapeutically effective amount of a telomerase transcriptional modulator of the invention. Pharmaceutical compositions of telomerase transcriptional modulators, or combinations of such species and/or with other pharmaceuticals in a pharmaceutically acceptable carrier or salt. Other pharmaceutical compositions of the invention comprise a telomerase transcription activator preparation.

The therapeutic agent can be provided in a formulation suitable for parenteral, nasal, oral, or other mode of administration.

In another aspect of the invention, buffered aqueous solutions comprising at least one telomerase-inhibitory or activating species of the invention at a concentration of at least 1 nM but not more than about 100 mM is formulated for administration, usually at a concentration of about 0.1 to 10 mM, typically by intravenous route, to a patient undergoing anti-neoplastic or anti-helminthic chemotherapy. The buffered aqueous solutions of the invention may also be used, typically in conjunction with other established methods, for organ culture, cell culture, delivery to transformed cells, and ex vivo cellular therapies. Nonaqueous formulations, such as lipid-based formulations are also provided, including stabilized emulsions. The telomerase-modulating compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

The telomerase-modulating species of the present invention can be administered as a pharmaceutical composition comprising the compound in combination with a pharmaceutically acceptable excipient. Such excipients include water, saline, Ringer's solution, dextrose solution, and solutions of ethanol, glucose, sucrose, dextran, mannose, mannitol, sorbitol, polyethylene glycol, phosphate, acetate, gelatin, collagen, and the like. One may additionally include other suitable preservatives, stabilizers and antimicrobials, antioxidants, buffering agents and the like. A thorough discussion of pharmaceutically acceptable excipients is available in *Remington's Pharmaceutical Sciences*, 19th Ed., (1995) Mack Publishing Co. Typically, a modulator of the invention is formed in a pharmaceutical dosage form comprising an excipient and not less than 1 µg nor more than about 100 grams of at least one telomerase-modulating species of the invention. In another aspect of the invention, buffered aqueous solutions comprising at least one telomerase-modulating species of the invention at a concentration of at least 1 nM but generally not more than about 100 mM is formulated for administration, usually at a concentration of about 0.1 µM to 10 mM, typically by intravenous route or via in infusion pump for localized delivery (e.g., to a solid tumor) or sustained dosing.

Alternatively, one may incorporate or encapsulate the telomerase-modulating agents in a suitable polymer matrix, liposome or membrane, thus providing a sustained release delivery device suitable for implantation near the site to be treated locally. In general, with sustained release delivery, the formulations are constructed so as to achieve a constant concentration which will be bioequivalent to about 100 times the serum level of 10 times the tissue concentration. Nonaqueous formulations, such as lipid-based formulations are also provided, including stabilized emulsions.

The amount of telomerase-modulating agent required to treat any particular neural disorder will of course vary depending on the nature and severity of the disorder, the age and condition of the patient, and other factors readily determined by one of skill in the art. Suitable dosages are from 1 ng/kg to about 1000 mg/kg, more preferably 1 µg/kg to about 100 mg/kg.

K. Purification of Mammalian Telomerase Protein Component

Mammalian telomerase protein component can be purified by the method disclosed in U.S. patent application Ser. No. 08/288,501, filed 10 Aug. 1994 from telomerase-expressing cells, such as HT1080 cells, 293 cells, and other suitable immortalized cell lines. For example and not limitation, human telomerase can be purified from cell extracts. Mammalian telomerase extracts can be stripped of the telomerase RNA component, if desired, by treatment with an RNAse activity or other suitable means to dissociate and/or degrade the telomerase RNA component while leaving telomerase protein component substantially intact and capable of reconstitution with addition of exogenous telomerase RNA component, or a mimetic thereof such as may be produced recombinantly or the like. The telomerase protein component thus purified, and optionally stripped of endogenous telomerase RNA component, can be used in the agent screening assays described herein, and for other uses.

L. Position Effect Modulatory Agents

Telomeric repeats organize a change in chromatin structure that propagates thousands of base pairs into the subtelomeric region. This altered telomeric chromatin (termed chromatel) is believed to be the actual regulator of genes that control life span. In the Chromatel Model of Cellular Senescence, chromatel extension is closely linked to the number of telomeric repeats, so as telomeres shorten with replicative senescence, chromatels also shorten. As with other chromatin position effects, many other proteins and factors besides telomere length affect the extension of chromatels. According to the Chromatel Model, therefore, heterochromatin proteins as well as histone and DNA modification affect chromatel extension and, by implication, cell life span.

As an example of histone modifications, histone hyper-acetylation is known to weaken heterochromatin position effects and should cause a shortening in the chromatel for the same size telomeres. Histone hyper-acetylation is believed to accelerate senescence. Inhibitors of histone poly-ADP-ribosylation, which stabilize chromatel extension, lead to extended cell life span.

Evidence that telomere length is linked to changes in chromatin acetylation can be shown by inducing hyper-acetylation in telomerase-positive cell lines (HT1080 and 293) and then checking telomere length after some 10–30 doublings. The cell will attempt to maintain chromatel length by activating telomerase and lengthening telomeres to counteract the shortening of chromatels by hyper-acetylation. Telomere lengthening in cells with hyper-acetylated histones indicates therapeutic approaches (e.g. cells can be treated with an inhibitor of histone deacetylase and extend their telomeres to extend life-span, such as in transgenic mice).

In view of this, a novel therapeutic strategy for telomerase inhibition in cancer is possible: telomerase inhibition combined with a suppressor of chromatin position effects kills cancer cells much faster than telomerase inhibition alone. Cancer cells are still preferentially affected by this two-drug treatment, because histone acetylation only induces premature senescence in dividing cells (chromatels shortened by histone acetylation are presumably fixed by changes in DNA methylation during division).

Therefore, it is desirable to screen for genes or small molecules that affect chromatin position effects and then test their effect on cell life span.

Cells wherein chromatin position conditionally represses expression of a reporter polynucleotide that is integrated or homologously recombined into a chromosomal locus can be made. A reporter polynucleotide comprises a polynucleotide sequence encoding a selectable drug marker gene (e.g., neo, HPRT, etc.) under transcriptional control of an operably linked transcription regulatory region which comprises an hTR promoter or which typically is not derived from a mammalian telomerase gene and often is substantially constitutively active in a mammalian cell line (e.g., an SV40 large T Ag promoter/enhancer, GAPDH promoter. etc.). The reporter polynucleotide is introduced into a cell population, such as a cultured cell line or organism, and the cell population is cultured in the presence of an agent predetermined to reduce position effect (e.g., 0.5 mM sodium butyrate) and the cell population is exposed to a positive selection agent (e.g., G-418 for neo$^R$; HAT medium for positive selection of HPRT-expressing cells; gancyclovir for tk:-expressing cells, and the like) and the population is selected for cells expressing the presence of the drug marker. The selected population is cultured in the substantial absence of said agent predetermined to reduce position effect, and the cell population is exposed to a negative selection agent (e.g., FIAU for tk-expressing cells, 6-thioguanine for HPRT-expressing cells) which selects for cells which substantially lack expression of the drug marker.

The resultant cell doubly-selected subpopulation is enriched in cells which have integrated reporter polynucleotides exhibiting position effect, wherein the reporter polynucleotide is expressed under conditions where position effect is relieved (e.g., 0.5 mM sodium butyrate), but is substantially transcriptionally repressed by position effect in the absence of agents which relieve position effect. The doubly-selected cell population typically comprises a collection of cell clones which have integrated reporter polynucleotides into position effect-sensitive chromatin regions; these cells are termed position effect reporter cells. In a variation, individual clonal progeny of position effect reporter cells are selected from the doubly-selected cell population for subsequent use.

Agents which modulate chromatin position effects on expression of a reporter polynucleotide that is integrated or homologously recombined into a chromosomal locus can be identified. Position effect reporter cells are cultured in conditions wherein the integrated reporter polynucleotide is substantially transcriptionally silent, the cells are exposed to an agent, and transcription of the reporter polynucleotide is determined (e.g., by positive selection, negative selection, RNA transcript analysis, or other phenotypic determination or assay). An agent which produces a detectable increase in transcription of the reporter polynucleotide as compared to the position effect reporter cells cultured in the absence of the agent is thereby identified as a position effect modulatory agent, and more specifically as position effect antagonists. In a variation, position effect cells are cultured under conditions where position effect is relieved (e.g., 0.5 mM sodium butyrate), the cells are exposed to an agent, and transcription of the reporter polynucleotide is determined (e.g., by positive selection, negative selection, RNA transcript analysis, or other phenotypic determination or assay). An agent which produces a detectable decrease in transcription of the reporter polynucleotide as compared to the position effect reporter cells cultured in the absence of the agent is thereby identified as a position effect modulatory agent, and more specifically as position effect agonists.

A cDNA expression library is introduced into a population of position effect reporter cells, whereby a library of position effect reporter cells is created wherein the position effect reporter cells individually express cDNA library members, which can be in either sense or antisense orientation, or a combination of sense and antisense orientations. In this embodiment, the introduced cDNA expression library member can serve as the agent and expressed cDNA library members which produce a detectable decrease or increase in reporter polynucleotide transcription as compared to cells lacking a cDNA library member are thereby identified as position effect antagonists or agonists, respectively. In a variation, a predetermined position effect modulator is added to a telomerase assay and the effect on telomerase activity is determined. In a variation, a predetermined position effect modulator is administered to a cell which does not express telomerase in the absence of the agent and the ability of the agent to induce detectable telomerase is determined. In a variation, a predetermined position effect modulator is administered to a telomerase-expressing cell and the ability of the agent to repress telomerase activity is determined.

In an embodiment, the agent is a polynucleotide, such as an antisense RNA transcribed from an antisense cDNA expression library member transfected into a position effect reporter cell.

For chromatin position-effect screening, the SV40 or hTR promoter can be operably linked to the coding region of the HPRT marker gene, whose expression can be selected for in HAT media or selected against in 6-thioguanine. Both the SV40 and hTR promoters appear sensitive to chromatin position effects, so the choice between these two promoters should be empirical, depending on which gives best results.

Stable transformants will be prepared using the HPRT expression vectors transfected into HPRT⁻ cells and selected in 0.5 mM sodium butyrate to induce histone hyper-acetylation that weakens position effects and HAT media to select for HPRT expression. Individual HPRT-expressing colonies will then be shifted to 6-thioguanine media without butyrate to select for low HPRT expressing cells in conditions where position effects are strengthened in the absence of histone hyper-acetylation. Clonal populations that can switch HPRT expression on or off in the presence or absence of butyrate will be selected as potential indicator cells for position-effect screening. If histone hyper-acetylation appears linked to telomere length, then the indicator cells can be tested for linkage to telomeres by incubating the cells with telomerase inhibitors that induce telomere loss. If telomerase inhibition causes a delayed reactivation of HPRT in some of the clones cultured without butyrate, then these clones would be the best indicator cells for chromatel position-effect screening (termed PES cells).

HPRT-switchable PES cells can be used in both gene and small-molecule screens for enhancers and suppressors of position effects. For example, to use the PES cells to screen for genes that suppress position effects, one would generate stable transformants of the PES cells by transfecting in a neo expression library containing antisense human gene tags (subtracted libraries with low levels of common sequences might be best) and by selection in HAT+G418 media in the absence of butyrate. DNA can be isolated from the colonies that grow out and the associated antisense human gene tags rescued by PCR amplification. The antisense tags that are pulled out in this screen can be added back to the PES cells to determine that the selected antisense tag was a real suppressor of position effects.

A special class of antisense genes that suppress position effects can be the telomerase proteins. Since antisense telomerase genes would only suppress position effects later as telomeres significantly shorten, a screen could be designed to catch this potential subclass of the position effect genes and rescue the clone before the cells die off from critically shortened telomeres. Like HPRT, URA3 is a gene marker that can be selected for and against to allow position effect cloning when the URA3 gene was placed in an appropriate position.

To select for genetic enhancers of chromatin position effects, one can generate stable transformants of the PES cells by transfecting in a neo expression library containing antisense human gene tags as before and then select in 6-thioguanine+G418 media in the presence of butyrate. This will select for antisense gene tags that enhance position effects or genes that in the sense orientation, would suppress position effects.

To screen for small molecules that enhance chromatin position effects, the PES cells will be cultured in 6-thioguanine in the presence of butyrate and various drugs to be tested. To screen for small molecule suppressors of chromatin position effects, the PES cells will be cultured in HAT media in the absence of butyrate and the various agents to be tested.

Any genes or small molecules that alter chromatin position effects can be tested for effects on cell life span or normal cells. Enhancers of position effects would be expected to lengthen life span while suppressors would be expected to shorten it. Suppressors of chromatin position effects could be tested along with inhibitors of telomerase to determine whether tumor cell killing can be accelerated by this two-drug strategy. These secondary screens should provide novel therapeutics for cancer and age-related diseases therapeutics.

The present invention provides novel inventions. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for determining whether an agent modulates the transcription of a mammalian telomerase gene, said mammalian telomerase gene comprising at least 20 nucleotides of SEQ ID NO:1, the method comprising the steps of determining the ability of an agent to modulate transcription of a polynucleotide transcription regulator sequence of said mammalian telomerase gene operably linked to a reporter sequence in a transcription assay; wherein said agent is determined to be a modulator of mammalian telomerase gene transcription if said agent is effective to produce a detectable increase or decrease in expression of a product encoded by said reporter polynucleotide sequence when said polynucleotide transcription regulator sequence of said mammalian telomerase gene is exposed to said agent as compared to a comparable transcription assay lacking said agent.

2. The method of claim 1, wherein the transcription assay comprises an in vitro transcription reaction.

3. The method of claim 1, wherein the transcription assay comprises using a stably or transiently transfected host cell.

4. The method of claim 1, wherein the transcription assay comprises using a transgenic animal having a genome.

5. The method of claim 1, wherein said mammalian telomerase gene is a mammalian telomerase RNA component gene.

6. The method of claim 5, wherein said mammalian telomerase gene is a human telomerase RNA gene (SEQ ID NO:1).

7. The method of claim 6, wherein said polynucleotide transcription regulator sequence is in the nucleotide sequence identified as SEQ ID NO:1.

8. The method of claim 6, wherein said polynucleotide transcription regulator sequence is in the polynucleotide sequence identified as SEQ ID NO:2.

9. The method of claim 6, wherein said reporter polynucleotide sequence encodes a gene for HPRT.

10. The method of claim 6, wherein said reporter polynucleotide sequence encodes a gene for HSV-tk.

11. The method of claim 6, wherein said reporter polynucleotide sequence encodes a gene for neoR.

12. The method of claim 6, wherein said reporter polynucleotide sequence encodes a gene for β-galactosidase.

13. The method of claim 6, wherein said reporter polynucleotide sequence encodes a gene for fluorescent protein.

14. The method of claim 6, wherein said reporter polynucleotide sequence encodes a gene for chloramphenicol.

15. The method of claim 6, wherein said reporter polynucleotide sequence encodes a gene for acetyltransferase.

16. The method of claim 6, wherein said reporter polynucleotide sequence encodes a gene for luciferase.

17. The method of claim 6, wherein said polynucleotide transcription regulator sequence includes nucleotides 1–1458 of SEQ ID NO:1.

18. The method of claim 6, wherein the transcription assay is carried out in vitro.

19. The method of claim 6, wherein the transcription assay comprises using a stably or transicnty transfected host cell.

20. The method of claim 6, wherein the transcription assay comprises using a transgenic animal.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 2426 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: -
         (B) LOCATION: 1..2426
         (D) OTHER INFORMATION: /note= "SauIIIA1-HindIII fragment
             containing hTR sequences as well as
             transcription regulatory sequences"

(xi) SEQUENCE DESCRIPTION: SEQ ID NO:1:

GATCAGTTAG AAAGTTACTA GTCCACATAT AAAGTGCCAA GTCTTGTACT CAAGATTATA      60

AGCAATAGGA ATTTAAAAAA AGAAATTATG AAAACTGACA AGATTTAGTG CCTACTTAGA     120

TATGAAGGGG AAAGAAGGGT TTGAGATAAT GTGGGATGCT AAGAGAATGG TGGTAGTGTT     180

GACATATAAC TCAAAGCATT TAGCATCTAC TCTATGTAAG GTACTGTGCT AAGTGCAATA     240

GTGCTAAAAA CAGGAGTCAG ATTCTGTCCG TAAAAAACTT TACAACCTGG CAGATGCTAT     300

GAAAGAAAAA GGGGATGGGA GAGAGAGAAG GAGGGAGAGA GATGGAGAGG GAGATATTTT     360

ACTTTTCTTT CAGATCGAGG ACCGACAGCG ACAACTCCAC GGAGTTTATC TAACTGAATA     420

CGAGTAAAAC TTTTAAGATC ATCCTGTCAT TTATATGTAA AACTGCACTA TACTGGCCAT     480

TATAAAAATT CGCGGCCGGG TGCGGTGGCT CATACCTGTA ATCCCAGCAC TTTGGGAGGC     540

CGAAGCGGGT GGATCACTTG AGCCCTGGCG TTCGAGACCA GCCTGGGCAA CATGGTGAAA     600

CCCCCGTCTC TACTAAAAAC ACAAAAACTA GCTGGGCGTG GTGGCAGGCG CCTGTAATCC     660

CAGCTACTCA GGAGGCTGAG ACACGAGAAT CGCTTGAACC CGGGAGCAGA GGTTGCAGTG     720

AGCCGAGATC ACGCCACTAG ACTCCATCCA GCCTGGGCGA AAGAGCAAGA CTCCGTCTCA     780

AAAAAAAAAA TCGTTACAAT TTATGGTGGA TTACTCCCCT CTTTTTACCT CATCAAGACA     840

CAGCACTACT TTAAAGCAAA GTCAATGATT GAAACGCCTT TCTTTCCTAA TAAAAGGGAG     900

ATTCAGTCCT TAAGATTAAT AATGTAGTAG TTACACTTGA TTAAAGCCAT CCTCTGCTCA     960

AGGAGAGGCT GGAGAAGGCA TTCTAAGGAG AAGGGGGCAG GGTAGGAACT CGGACGCATC    1020

CCACTGAGCC GAGACAAGAT TCTGCTGTAG TCAGTGCTGC CTGGGAATCT ATTTTCACAA    1080

AGTTCTCCAA AAAATGTGAT GATCAAAACT AGGAATTAGT GTTCTGTGTC TTAGGCCCTA    1140

AAATCTTCCT GTGAATTCCA TTTTTAAGGT AGTCGAGGTG AACCGCGTCT GGTCTGCAGA    1200

GGATAGAAAA AAGGCCCTCT GATACCTCAA GTTAGTTTCA CCTTTAAAGA AGGTCGGAAG    1260

TAAAGACGCA AAGCCTTTCC CGGACGTGCG GAAGGGCAAC GTCCTTCCTC ATGGCCGGAA    1320
```

-continued

```
ATGGAACTTT AATTTCCCGT TCCCCCCAAC CAGCCCGCCC GAGAGAGTGA CTCTCACGAG    1380

AGCCGCGAGA GTCAGCTTGG CCAATCCGTG CGGTCGGCGG CCGCTCCCTT TATAAGCCGA    1440

CTCGCCCGGC AGCGCACCGG GTTGCGGAGG GTGGGCCTGG GAGGGGTGGT GGCCATTTTT    1500

TGTCTAACCC TAACTGAGAA GGGCGTAGGC GCCGTGCTTT TGCTCCCCGC GCGCTGTTTT    1560

TCTCGCTGAC TTTCAGCGGG CGGAAAAGCC TCGGCCTGCC GCCTTCCACC GTTCATTCTA    1620

GAGCAAACAA AAAATGTCAG CTGCTGGCCC GTTCGCCCCT CCCGGGGACC TGCGGCGGGT    1680

CGCCTGCCCA GCCCCCGAAC CCCGCCTGGA GGCCGCGGTC GGCCCGGGGC TTCTCCGGAG    1740

GCACCCACTG CCACCGCGAA GAGTTGGGCT CTGTCAGCCG CGGGTCTCTC GGGGGCGAGG    1800

GCGAGGTTCA GGCCTTTCAG GCCGCAGGAA GAGGAACGGA GCGAGTCCCC GCGCGCGGCG    1860

CGATTCCCTG AGCTGTGGGA CGTGCACCCA GGACTCGGCT CACACATGCA GTTCGCTTTC    1920

CTGTTGGTGG GGGAACGCC GATCGTGCGC ATCCGTCACC CCTCGCCGGC AGTGGGGGCT     1980

TGTGAACCCC CAAACCTGAC TGACTGGGCC AGTGTGCTGC AAATTGGCAG GAGACGTGAA    2040

GGCACCTCCA AAGTCGGCCA AAATGAATGG GCAGTGAGCC GGGGTTGCCT GGAGCCGTTC    2100

CTGCGTGGGT TCTCCCGTCT TCCGCTTTTT GTTGCCTTTT ATGGTTGTAT TACAACTTAG    2160

TTCCTGCTCT GCAGATTTTG TTGAGGTTTT TGCTTCTCCC AAGGTAGATC TCGACCAGTC    2220

CCTCAACGGG GTGTGGGGAG AACAGTCATT TTTTTTTGAG AGATCATTTA ACATTTAATG    2280

AATATTTAAT TAGAAGATCT AAATGAACAT TGGAAATTGT GTTCCTTTAA TGGTCATCGG    2340

TTTATGCCAG AGGTTAGAAG TTTCTTTTTT GAAAAATTAG ACCTTGGCGA TGACCTTGAG    2400

CAGTAGGATA TAACCCCCAC AAGCTT                                        2426
```

(2) INFORMATION FOR SEQ ID NO:2:

(i) SEQUENCE CHARACTERISTICS:
        (A) LENGTH: 981 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..981
        (D) OTHER INFORMATION: /note= "PstI fragment containing hTR
            sequence"

(xi) SEQUENCE DESCRIPTION: SEQ ID NO:2:

```
CTGCAGAGGA TAGAAAAAAG GCCCTCTGAT ACCTCAAGTT AGTTTCACCT TTAAAGAAGG      60

TCGGAAGTAA AGACGCAAAG CCTTTCCCGG ACGTGCGGAA GGGCAACGTC CTTCCTCATG    120

GCCGAAATG GAACTTTAAT TTCCCGTTCC CCCCAACCAG CCCGCCCGAG AGAGTGACTC     180

TCACGAGAGC CGCGAGAGTC AGCTTGGCCA ATCCGTGCGG TCGGCGGCCG CTCCCTTTAT    240

AAGCCGACTC GCCCGGCAGC GCACCGGGTT GCGGAGGGTG GGCCTGGGAG GGTGGTGGC     300

CATTTTTTGT CTAACCCTAA CTGAGAAGGG CGTAGGCGCC GTGCTTTTGC TCCCCGCGCG    360

CTGTTTTTCT CGCTGACTTT CAGCGGGCGG AAAAGCCTCG GCCTGCCGCC TTCCACCGTT    420

CATTCTAGAG CAAACAAAAA ATGTCAGCTG CTGGCCCGTT CGCCCCTCCC GGGGACCTGC    480

GGCGGGTCGC CTGCCCAGCC CCCGAACCCC GCCTGGAGGC CGCGGTCGGC CCGGGGCTTC    540

TCCGGAGGCA CCCACTGCCA CCGCGAAGAG TTGGGCTCTG TCAGCCGCGG GTCTCTCGGG    600

GGCGAGGGCG AGGTTCAGGC CTTTCAGGCC GCAGGAAGAG GAACGGAGCG AGTCCCCGCG    660
```

-continued

| | | | | | |
|---|---|---|---|---|---|
| CGCGGCGCGA | TTCCCTGAGC | TGTGGGACGT | GCACCCAGGA | CTCGGCTCAC | ACATGCAGTT | 720 |
| CGCTTTCCTG | TTGGTGGGGG | GAACGCCGAT | CGTGCGCATC | CGTCACCCCT | CGCCGGCAGT | 780 |
| GGGGGCTTGT | GAACCCCCAA | ACCTGACTGA | CTGGGCCAGT | GTGCTGCAAA | TTGGCAGGAG | 840 |
| ACGTGAAGGC | ACCTCCAAAG | TCGGCCAAAA | TGAATGGGCA | GTGAGCCGGG | GTTGCCTGGA | 900 |
| GCCGTTCCTG | CGTGGGTTCT | CCCGTCTTCC | GCTTTTTGTT | GCCTTTTATG | GTTGTATTAC | 960 |
| AACTTAGTTC | CTGCTCTGCA | G | | | | 981 |